United States Patent [19]

Alexandre et al.

[11] Patent Number: 4,954,261

[45] Date of Patent: Sep. 4, 1990

[54] METHOD FOR EXTRACTING COMPOUNDS HAVING A HIGH ADDED VALUE FROM COMPLEX SOLUTIONS AND MEMBRANE DEVICE FOR IMPLEMENTING SUCH METHOD

[75] Inventors: Stéphane Alexandre, Saint Etienne Du Rouvray; Michel Thellier, Darnetal; Jean-Claude Vincent, Cleres, all of France

[73] Assignee: Centre National de la Recerche Scientifique - Cnrs, Paris, France

[21] Appl. No.: 309,765

[22] PCT Filed: May 22, 1987

[86] PCT No.: PCT/FR87/00180

§ 371 Date: Jan. 30, 1989

§ 102(e) Date: Jan. 30, 1989

[87] PCT Pub. No.: WO87/07294

PCT Pub. Date: Dec. 3, 1987

[30] Foreign Application Priority Data

May 30, 1986 [FR] France ............... 86 07792

[51] Int. Cl.$^5$ ............................. B01D 63/08
[52] U.S. Cl. ..................... 210/638; 210/647; 210/321.75; 210/321.84
[58] Field of Search .............. 210/651, 748, 222, 223, 210/243, 321.72, 321.75, 321.84, 637, 634, 638, 641, 644, 645–647, 649–654

[56] References Cited

U.S. PATENT DOCUMENTS 4,163,714 8/1979 Gregor ................. 210/651

OTHER PUBLICATIONS

E. Seiegny et al., "Two Enzyme Active Transport in Vitro with pH Induced Asymmetyrical Functional Structures. I. The Model and its Analytical Treatment", p. 214, ref.: 199369a, & Biophys. Chem. 1980, 12(1), 93–106 (Eng), Chemical Abstracts, vol. 93, No. 21, 24, Nov. 1980 (Columbus, Ohio, US).

J. C. Vincent et al., "Ion Transport by Asymmetrical Functional Membrane Model", Chemical Abstracts, vol. 99, No. 17, 24 Oct. 1983 (Columbus, Ohio, US); p. 237, ref.: 135631w, & Stud. Phys. Theor. Chem. 1983, 24(Phys. Chem. Transmentor. Ion Motions), 123–8 (Eng).

J. C. Vincent et al., "Active Transport of Glucose in Vitro Illustration of Asymmetrical Functional Structures and of Allotopia", Chemical Abstracts, vol. 90, 13, Mar. 26, 1979 (Columbus, Ohio, US), pp.148, ref.: 98692h, & Collop. 1, Int. C.N.R.S. 1976 (Pub. 1977), 258; (Exchanges Ioniques Transmembr. Veg.), 147–153 (Eng).

GB, A, 2164663 (KAO Co.) Mar. 26, 1986, Voir Revendications 1,2; Figures 1, 2, 13, 15, 16.

*Primary Examiner*—Frank Sever
*Attorney, Agent, or Firm*—Browdy and Neimark

[57] ABSTRACT

Method and device for the selective extraction of compounds, particularly biochemical compounds having a high added value, from a complex solution. The method makes use of a monoenzyme reactive membrane system (3, 4, 5, 6) in a liquid medium, at the interfaces of which an electrochemical potential gradient of one of the reagents creates asymmetrical conditions which force the reversible reaction catalyzed by the reactive membrane system to operate in opposite directions on either side of said system, the passage of the compound to be extracted from one side to the other being favored by the presence on both faces of said system of barriers (5) which confine a compound other than the compound to be extracted. Device for implementing such method. Application to the extraction of compounds which are interesting from a biochemical point of view by concentration and accumulation on one side of the membrane system.

17 Claims, 5 Drawing Sheets

METHOD FOR EXTRACTING COMPOUNDS HAVING A HIGH ADDED VALUE FROM COMPLEX SOLUTIONS AND MEMBRANE DEVICE FOR IMPLEMENTING SUCH METHOD

FIELD OF THE INVENTION

The present invention relates to a method for extracting compounds of high added value, and in particular biochemical compounds, from complex solutions and to a device provided with a reactive membrane, suitable for performing this method.

BACKGROUND OF THE INVENTION

In biology, many trans-membranal passages of molecules or of ions occur with a saturation kinetics and are attributed to an enzymatic mechanism of the permease type. When the membranal system is capable of causing the molecule or the ion transported to pass from one side where it occurs at a low electrochemical potential to the other side where its electrochemical potential is higher, the mechanism which constitutes an active transport necessitates the presence of an asymmetry. Thus, the study of certain ion or molecular pumps has shown an asymmetric location of the reaction sites within membranes, whether this be in the structural asymmetry of a protein, like for example its organization in sub-units, certain of these sub-units being on the inner surface of the membrane, others on the outer surface, as for ATPase, or this be in the structural asymmetry of the transport system, which may be multi-enzymatic or comprise several protein complexes or the like located at quite specific plates of the membrane as in the chain of respiration, photo-systems, etc . . .

The in vivo study of these mechanisms always remains of great complexity. Modelization, in using simpler artificial systems in which the number of parameters is limited, enables complex biological phenomena to be approached, whilst realizing active transports of ions or of molecules. Thus there have been proposed in the prior art active transport models in which the asymmetry necessary for the vectorial transport is structural, that is to say it forms an asymmetric distribution of enzyme molecules in the membrane [cf THOMAS & CAPLAN "Membrane Separation Processes", Ed. MEARES, ELSEVIER, Amsterdam, Netherlands (1976), 351].

One of the inventors has shown that it is possible to replace this permanent structural asymmetry by a functional asymmetry in which the reactions are activated or inhibited by an effector [(J.C. VINCENT, These de Doctorat es Sciences, Rouen, France (1980)]; this functional asymmetry has been demonstrated in a model constituted by a membrane with two enzymes distributed uniformly, in which the enzymatic functions are distributed in space, by introducing and by maintaining a pH gradient on the membrane (SELEGNY and VINCENT, BIOPHYS. CHEM. 12 (1980) 93-106 and 12 (1980) 107-113)]. A publication of the CNRS Colloquium No. 258 (1976) on TRANSMEMBRANAL IONIC EXCHANGES IN PLANTS entitled "ACTIVE TRANSPORT OF GLUCOSE IN VITRO, ILLUSTRATION OF ASYMMETRICAL FUNCTIONAL STRUCTURES AND OF ALLOTOPIA" appearing under the signature of J.C. VINCENT, E. SELEGNY and Y. describes an active transport membrane of glucose showing this type of functional asymmetry. This active membrane is obtained by casting an agarose gel containing hexokinase and acid phosphatase into a film which is treated with glutaraldehyde and which therefore contains the immobilized enzymes, distributed homogeneously. On the sides of the active membrane are placed structures constituting barriers bearing negative charges (which "barriers" are named "valves" in this publication), which are of agarose containing polyacrylic acid and which have the purpose of avoiding the diffusion of charged glucose-phosphate ions, through the active membrane see also the article entitled "TWO ENZYME ACTIVE TRANSPORT IN VITRO WITH PH-INDUCED ASYMMETRICAL FUNCTIONAL STRUCTURES - I - THE MODEL AND ITS ANALYTICAL TREATMENT" by E. SELEGNY and J.C. VINCENT in BIOPHYSICAL CHEMISTRY 12 (1980) 93-106.

The principle of the active transport model rests on the existence of a plurienzymatic reaction cycle of which the shortest is a bienzymatic system of the type

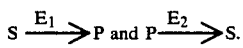

$$S \xrightarrow{E_1} P \text{ and } P \xrightarrow{E_2} S.$$

The two enzymes $E_1$ and $E_2$ of the cycle must then be influenced differently by an effector so that when they are inserted into a membranal structure traversed by a gradient of this effector, their activities are distributed along this gradient, ending in a functional structure with two layers. In the first layer, S is consumed, it enters therefore by diffusion from the donor compartment D towards the membrane and is converted into P by $E_1$, the product P diffusing into the membrane is again converted into S in the second activity layer $E_2$; the excess of S is then removed from the membrane by diffusion towards the receiver compartment R. The stoichiometry of this active transport is ensured by the symmetrical presence of "barriers" confining the compound P to the intramembranal space.

The principal drawback of this model is the necessity to find adequate enzymatic pairs, the hexokinase-phosphatase system being one of the rare examples of enzymatic pairs capable of functioning conjointly in cyclic manner.

As is known, the majority of chemical reactions are reversible: if a reaction involves two compounds A and B, there is constant competition between the two elemental reactions A ΔB and B→A and the apparent reaction velocity corresponds to the difference between the velocities of the two elemental reactions.

When an enzyme catalyzes a chemical reaction, it simultaneously increases the velocities of the two elemental reactions. Thus, reversible reactions are frequent in enzymology. May be mentioned, for example, proteases which, in aqueous media, catalyze the decomposition of peptides which also catalyze, in non-aqueous media, the synthesis of peptides. The majority of dehydrogenases belong to this group and have a great advantage since the reactions in the two directions can take place in the same aqueous medium.

The present invention is based on the combination of the use of the reversibility of many reactions catalyzed by a single and same enzyme and the application of prior studies mentioned above, in which one of the inventors has participated, by producing the reaction cycle of the active transport model by the two elemental reactions of the reversible reaction and by using a reagent whose gradient acts directly by the law of mass action on the reaction, to produce the asymmetry.

The present invention is again distinguished from the preceding studies described concerning the bienzymatic models in that the method only necessitating a single enzyme facilitates manufacture, and reduces the cost of utilization, eliminates the problems of compatibility of the enzymatic molecules with one another and simplifies the conditions of use.

An object of the present invention is a method for the selective extraction of a compound with a high added value, and particularly of a biochemical compound, from a complex solution, characterized in that there is employed to carry out said extraction, a monoenzymatic reactive membrane system, suitable for catalyzing a reversible reaction which is placed in a liquid medium, in that at the membranal system/liquid medium interfaces asymmetric conditions are created by means of an electrochemical potential gradient of one of the reagents, which asymmetric conditions force the reversible reaction to operate in one direction on one side of the membranal reagent system and in the other direction on the other side, in that the compound to be extracted effects, consequently, a reaction loop which causes it to pass from one side of the reactive membranal system to the other side, and its accumulation on this side are facilitated by the presence on the two surfaces of said system of a layer constituting a specific barrier adapted to confine in the intramembranal space at least one of the compounds other than the compound to be extracted.

By "barrier" is meant a structure which prohibits the passage of the compound to be confined into the intramembranal space; the means of prohibition of the passage are selected as a function of the nature of the compound to be confined. In particular, if the compound to be confined is charged, they may be constituted by an overall charge of opposite sign borne by the barrier; if the compound to be confined is a large molecule, they may be constituted by a microporous film; if the compound to be confined shows a given hydrophobicity, they may be constituted by a substance conferring on the barrier a hydrophobicity of opposite nature.

Consequently, the ratio of the diffusion coefficients compound to be extracted/compound to be confined in the intramembranal space is $>>1$.

SUMMARY OF THE INVENTION

The Inventors have found that it is possible to ensure active transport or facility of the molecule by using a single enzyme instead of the two applications up to now. In fact, in the prior art it was sought to imitate the biological system by introducing asymmetry into the structure of the catalyst, and more specifically by creating asymmetry by acting on the enzymatic catalysts themselves, either by distributing asymmetrically the enzymatic molecules in the membranal structures, or by distributing their activities asymmetrically by an effector gradient (proton or the like, which modifies the reaction but does not necessarily participate therein). On the other hand, according to the invention, the Inventors have found that the asymmetry sought may be obtained not by acting on the enzymatic catalysts, but by acting on the chemical reaction itself, by the law of mass action, that is to say on the concentrations of the reagents whilst the enzymatic catalyst, henceforth alone no longer has to take part to form the asymmetry and only takes part through its specificity and its membranal location.

Thus in the monoenzymatic membranal system according to the invention, the molecular heterogeneity of the two enzyme systems has disappeared and this goes contrary to the biomimetic considerations by which it would be desirable to preserve, as in living matter, a certain heterogeneity or molecular structural asymmetry to ensure an active transport.

The present invention is distinguished from the work previously described concerning bienzymatic models in that the method employs a single enzyme to produce the two directions of the reaction $A \rightleftarrows B$. This fact is fundamental since it introduces the idea of reversibility of the reaction, an idea completely absent from the work of the prior art, but especially because it considerably extends the scope of this extraction method:

The fact of bringing into play a single enzyme has a considerable advantage since it permits a very wide choice among existing enzymes and hence permits extractions of very varied molecules, whilst in the two enzyme models where each catalyses a part of the cycle ($A \rightarrow B$ then $B \rightarrow A$), the difficulty resides in the very restricted choice of such pairs of enzymes accepting the same substrates, and consequently, in the very limited possibility of active transports of some molecules.

(1) The method can operate when there is a reversible enzymatic reaction between at least three reagents, the first which it is desired to extract, the second playing the role of reagent to which a gradient is applied and the third which it is desired to confine to the intramembranal space. The process is then an active transport.

(2) The method can be extended to an enzymatic reaction with at least two reagents, of the type $A \rightleftarrows B$ by applying the chemical potential gradient to the compound that it is desired to extract, itself. The energy source is then the dissipation of this gradient and the process is a facilitated transport, which will then increase selectively the speed of passage through the membrane, of the compound to be extracted.

The method enables in this case the extraction but not the concentration of the species concerned.

(3) For other uses and whatever the number of reagents of the reaction, the method may also be used on condition of limiting the process to the formation and decomposition of the enzyme-compound complex to be extracted $E + A \rightleftarrows EA$, the enzyme itself, in free or complexed form, playing the role of the substance confined in the membrane and the gradient can be established either by modifying one of the forms of the enzyme in the membrane, in which case this gradient can be obtained by an effector gradient and particularly protons, the process then being an active transport permitting the concentration of the compound to be extracted, or by modifying the compound to be extracted itself, in which case the process is a facilitated transport and it is only possible to accelerate selectively the diffusion of the compound to be extracted.

According to an advantageous embodiment of the method according to the present invention, when the reaction involves at least three reagents, namely a compound to be extracted, at least one co-reagent and at least one compound intended to be confined in the intramembranal space defined by the membranal system, the electrochemical potential gradient of the co-reagent or of one of the co-reagents is established for a given equilibrium constant $K_{eq}$, by adjusting the electrochemical potentials to different values in the receptor and donor compartments defined by the membranal system, on each side of the latter, so that the ratio K given by the law of mass action, in which the concentration of the compound to be extracted is in the denominater, is $K < K_{eq}$ on the donor side and
$K > K_{eq}$ on the receiver side.

According to another advantageous embodiment of the method according to the present invention, when the reaction involves protons, these protons are advantageously used as reagent of which it is desired to establish the gradient, by adjusting the donor and receptor compartments situated on each side of the membranal system, to different pHs.

According to yet another advantageous embodiment of the method according to the present invention, when the reaction involves two reagents, namely a compound to be extracted and a reagent, a complex is formed between the compound to be extracted and the enzyme, the enzyme and the enzyme-compound complex are confined in the intramembranal space and an intermediate gradient of a suitable effector is established, such especially, as a pH gradient, which intermediate gradient causes in the intramembranal space, the establishment of an active free enzyme gradient, which is the desired electrochemical potential gradient.

In accordance with the laws of diffusion, the speed of extraction of the membranal system is inversely proportional to the square of the thickness of said system and it is proportional to the diffusion coefficients of the compounds through said system.

It is an object also of the present invention to provide a deviCe for the selective extraction of a compound with high added value, and particularly of a biochemical compound, from a complex solution, of the type comprising a cell subdivided into two compartments by a reactive membrane system comprising a membranal structure bearing enzymatic catalysts which confer on it an enzymatic activity and provided on its two surfaces, with barrier layers suitable for preventing the passage through said active membrane, of substances other than the compound to be extracted, which device is characterized in that the active membrane is constituted by a thin layer of a suitable gel and carries a single enzymatic catalyst, and wherein the barrier layers are structures which introduce a difference in mobility through the reactive membrane system, between the compound to be extracted, and at least one of the other reagents present, other than the compound to be extracted.

According to an advantageous embodiment of the device according to the present invention, the latter is characterized in that the cell is of the closed reactor type favorable to discontinuous operation.

According to another advantageous embodiment of the device according to the present invention, the latter is characterized in that the cell is of the continuous flow open reactor type, favorable to continuous operation.

According to an advantageous embodiment of the device according to the present invention, the enzymatic catalyst is retained in the membrane which carries it by the arrangement on each of the two surfaces of said membrane, of a microporous film.

According to another advantageous embodiment of the device according to the present invention, the enzymatic catalyst is fixed by covalent bonds in the membrane which bears it.

For carrying out the present invention, the procedure is as follows:

1°—Case of a three reagent reversible reaction, catalysed by an enzyme E:

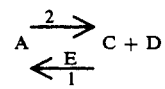
(1)

If the concentrations of A and C are given, D has an equilibrium concentration determined by the law of mass action:

$$K_{eq} = \frac{[C]_{eq} \times [D]_{eq}}{[A]_{eq}} \quad (2)$$

If [D] is greater than or less than the equilibrium concentration the reaction is displaced in one direction or the other, so as to satisfy the equation (2), that is to say if $[D] < [D]_{eq}$, to produce D by favouring the reaction to go A→C+D, and if $[D] > [D]_{eq}$, to consume D favouring the back reaction C+D→A.

Namely always the reversible reaction (1) and the concentrations of A, C and D according to FIG. 1 appended.

If a gradient of D is established through the member, $[D_1]$ being $> ]D]_{eq}$, there is displaced to the left of the membrane the reaction in the direction 1: C→A, and to the right of the membrane, as $[D_2] < [D]_{eq\ 1}$, it is displaced in the direction 2 A→C.

If, in addition, there are placed on each side of the membrane "barriers" almost impermeable to C, according to the appended FIG. 2, in which the membrane is denoted by the reference 6 and the barriers are denoted by the reference 5, the reagent A placed to the right of membrane, penetrates therein. Then, A→C (cf FIG. 1), and C cannot pass through the right barrier. It will therefore diffuse towards the left barrier, where then C→A and A passes through and finds itself again in the lefthand compartment which is enriched in A: there is active transport of A from right to left of the membrane.

2°—Case of a reversible reaction with more than three reagents: the concentrations of the other reagents X, Y, Z, etc, take part in the same way in the law of mass action to define the equilibrium constant $K_{eq}$. These co-reagents must be present in the system or at least in the active membrane. According to their concentrations, to $K_{eq}$ there corresponds an equilibrium concentration $D_{eq}$ of the compound of which it is desired to establish the gradient, the values of $D_1$ and $D_2$ are then selected as previously on each side of this value $D_{eq}$.

3°—Case of a reversible reaction with two reagents A"C: the equilibrium constant $K_{eq}$ equals $$K_{eq} = \frac{[C]_{eq}}{[A]_{eq}},$$

the reaction will be displaced in the membranal layer where $[A] > ]A]_{eq}$, by favouring the forward reaction A→C, and in the other layer where $[A] < [A]_{eq}$ by favoring the back reaction C→A. In addition to the transport of the compound A by diffusion, there is established in the membrane a selective destruction-production succession of this compound A resulting in a facilitated transport of A and hence in its extraction selectively.

where the concentration of alcohol is fixed and large, hence does not play any part, ADH denotes the alcohol-dehydrogenase
NADH is the compound A above to be transported
NAD+ is the compound C blocked by the barriers
H+ is D, namely the compound of which =gradient is imposed.

The membrane is advantageously a gelified agarose membrane, lined with a microporous film such as a "Millipore" film for example, to prevent the "leakage" of the enzyme which is not fixed in the membrane by covalent bonding, being however understood that the enzyme can also be fixed to the membrane by covalent bonding.

The "barrier" may advantageously be constituted by a polymer not available in commerce, developed in the laboratory, partially quaternized, Q-P(TDAE), which shows for the NAD+a permeability one hundred times less than for NADH [Q-P(TDAE) or "partially quaternized poly(thio-1-(N,N-diethylaminomethyl)ethylene)"]; this compound and its preparation are described in an Article which appeared in POLYMER JOURNAL, 12. N° 2, pages 113–124 (1980)].

Besides the foregoing features, the invention comprises still other features, which will emerge from the description which follows.

BRIEF DESCRIPTION OF THE DRAWINGS

The invention will be better understood by means the additional description which follows, which refers to examples of practising the method according to the present invention, and to the accompanying drawings in which.

It must be well understood, however, that these examples of practice, these drawings and the corresponding descriptive parts, are given purely by way of illustration of the invention, of which they do not constitute a limitation in any way.

DETAILED DESCRIPTION OF THE INVENTION

EXAMPLES

EXAMPLE 1Extraction of NADH from a complex solution by means or a monoenzymatic reactive membrane active transport system As is known, conventional metabolic cycles, such as the Krebs cycle, glycolysis, fermentation, the respiratory chain, use dehydrogenases to catalyze the oxidation of NADH (or nicotinamide-adenine-dinucleotide, reduced form) into NAD+(nicotinamide-adeninedinucleotide, oxidized form), in the presence of an oxidizing agent, as well as the reduction of the NAD$^{30}$ into NADH in the presence of a reducing agent (or their phosphorylated forms).

It has long been known that the reduction of NAD$^{30}$ acidifies the reaction medium by producing a proton, whilst the oxidation of NADH consumes a proton in accordance with the reversible reaction:

NAD$^{30}$ +RH$_2$ NADH+H$^+$+R where RH$_2$ is a reducing agent.

Alcohol-dehydrogenase extracted from yeast (yADH, EC 1.1.1.1.) catalyzes preferentially the reversible reaction of oxidation-reduction of the pair ethanol-/acetaldehyde:

Whilst the optimal pH of the oxidation reaction of the NADH, which consumes a proton, is of the order of 6, the optimal pH of the reduction reaction of the NAD$^{30}$, which produces a proton, is of the order of 8.3.

Figure 1:
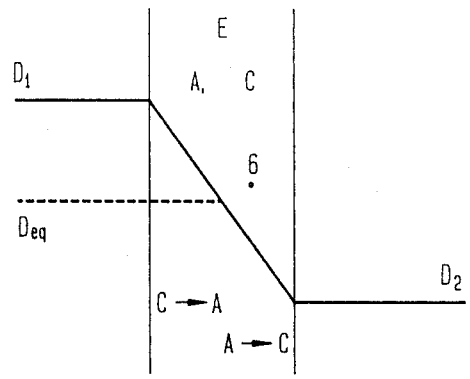
Figure 2:
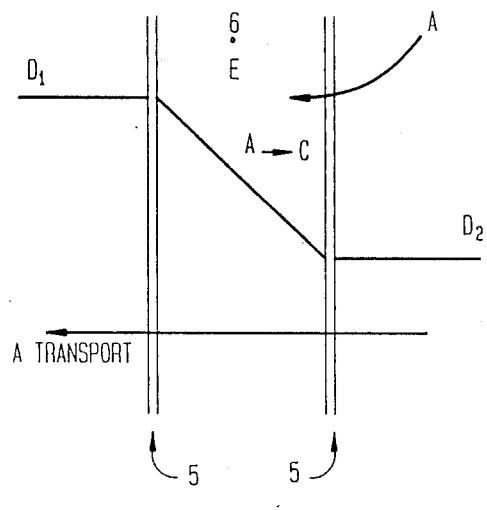
Figure 3:
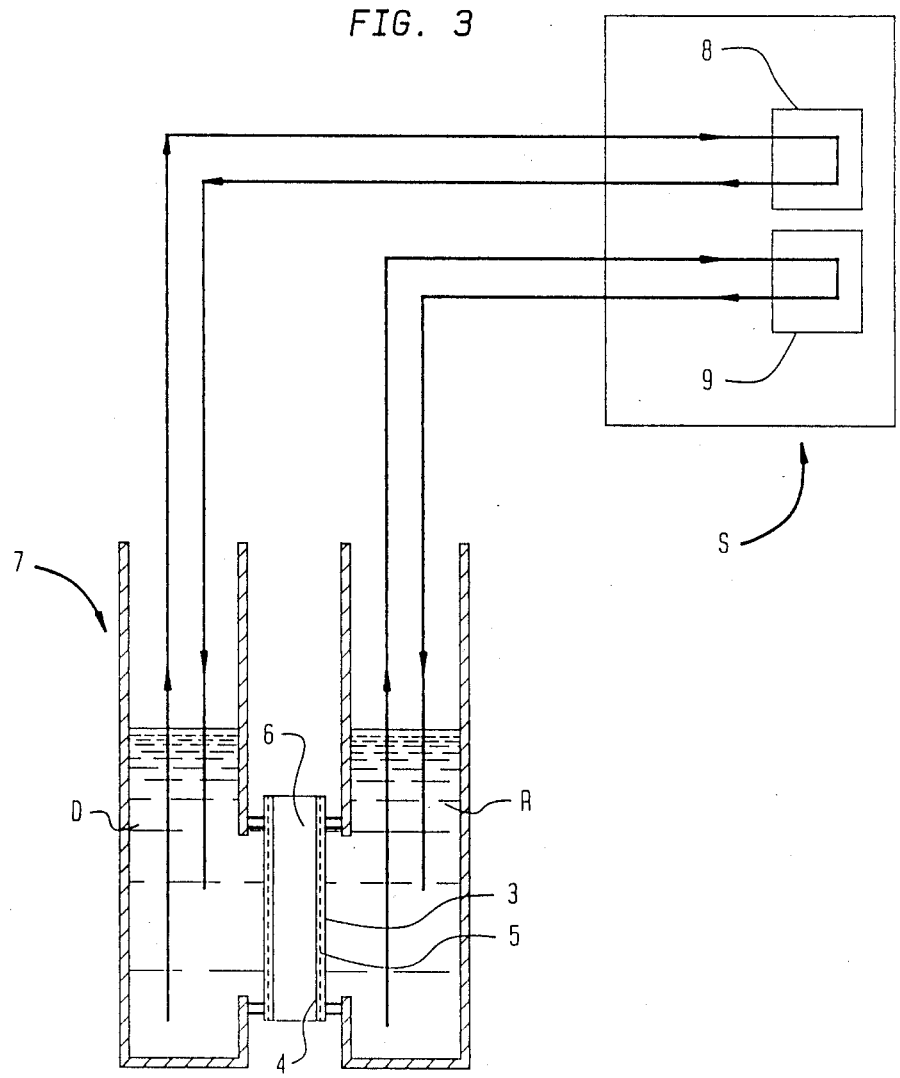
FIGS. 3 and 5 are diagrammatic drawings, in vertical section, of a selective extraction device for a compound with high added value, by means of a monoenzymatic reactive membrane system, according to the invention.

The fact that the oxidation reaction of the NADH takes place in a pH zone below that in which the reduction reaction of the NAD$^{30}$ occurs is used as follows, in accordance with the present invention:

The ADH is distributed homogeneously in a thin membrane (of the order of 1 mm thickness), 6, in 3.5% agarose gel in water, so that the gel contains 210 units (0.6 mg) of yADH (A 3263 provided by SIGMA) for 0.2 ml of gel. The membrane is inserted (cf FIG. 3) between two "barriers" of which each is constituted by a very thin film, 5, of agarose containing 10 mg of 14% Q-P(TDAE), which is permeable to the NADH and substantially impermeable to the NAD+. The yADH may be fixed to the agarose membrane by covalent bonding by means of glutaraldehyde, for example, or it may be simply distributed in the membrane without it being fixed to it, in which case it is advantageous to retain the enzyme in the membrane 6 by means of a microporous membrane (for example of Millipore type, of porosity 0.025 μm) 3,4. The composite membrane 3,4,5 has a thickness of about 0.3 mm. The reactive membrane system 3,4,5,6 so formed is placed in position in a cell 7 in 15 which it defines two compartments, the compartment D (donor) and the compartment R (receiver), fluid-tight with respect to one another. The two compartments D and R, contain initially the same buffered solution (phosphate buffer 20 mM) of all the components necessary o for the oxidation-reduction reactions: ethanol (2 M), acetaldehyde (1 mM) and NADH (0.5 mM) with the exception of the NAD$^{30}$ Each of the compartments contains 10 ml of liquid for a membrane surface in contact with the solutions of 2 cm$^2$ each time. In the initial phase t=0, the pH of the compartments D and R is adjusted respectively to 7.2 and 8.6 by means of a pH-stat. Two circulation cells 8,9, of a spectrophotometer S enable measurement continuously of the optical density at 340 nm of the solutions contained in each of the compartments D and R, which varies as a function of the concentration in NADH in each of the two compartments.

Figure 4:
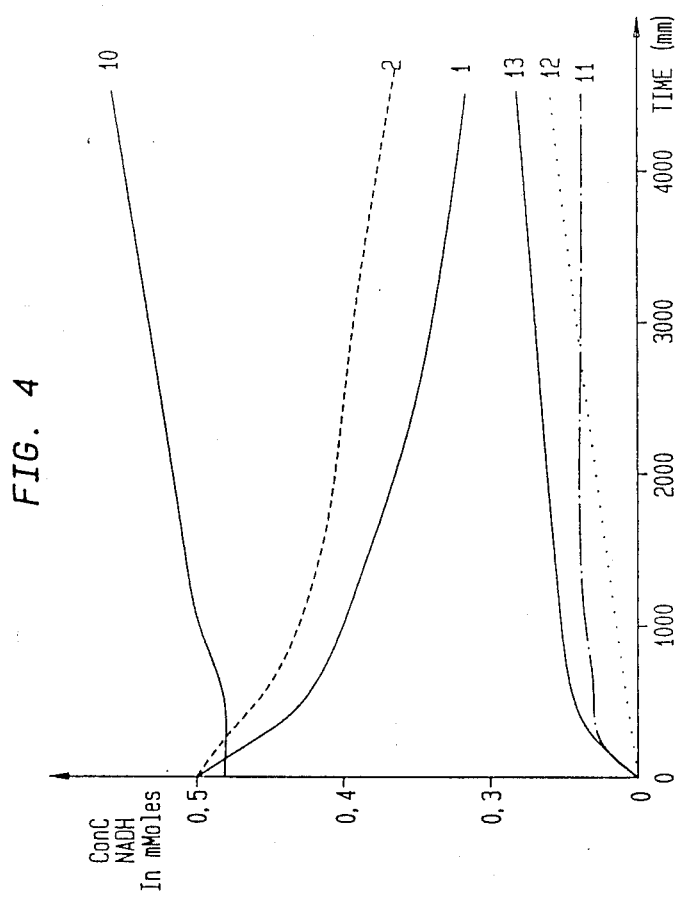
FIGS. 4 and 6 show graphs in which the curves 1, 2 and 10 to 13 (FIG. 4) and 13 to 17 (FIG. 6) measure respectively the variations of the concentration of the NADH in a device of the type shown in FIG. 3.

The curves of the concentrations of the NADH in the two compartments read as a function of time, are shown in accompanying FIG. 4: they reveal the existence of two phases: the first phase, which corresponds to an asymmetric diminution of the concentrations of NADH in the two compartments, constitutes in fact, the filling phase of the membrane (initially empty of NADH and of NAD$^{30}$) as well as the progressive establishment of the concentration profiles (H+, NADH, NAD$^{30}$) within the membrane.

The second phase constitutes the active transport proper characterized by the fact that the concentration of NADH increases in the receiver compartment R where the concentration of H+ions is lowest (at pH=8.6) and diminishes in the donor compartment D (at pH =7.2). These two phases are shown by the curves 1, 2 and 10 to 13 of which the first, 11, shows the filling curve of the membrane with AND, whilst the curve 12 shows the degradation curve of the NADH, and the curve 13 the sum of these two curves; the curves 1 and 2 show the 15 development as a function of time of the concentration of the NADH in the donor compartment at pH 7.2 and the development of this same concentration taking into account the non-enzymatic degradation of the NADH at pH 7.2 (curve 12), curve 10 shows the development as a function of time of the concentration of the NADH in the receiver compartment at pH 8.6.

In fact, at the same time as this looped oxidation-reduction reaction and by reason of the long duration of the experiment, there occurs a slow pH-dependant degradation of the NADH. This degradation is greater in the compartment where the pH is equal to 7.2.

By taking into account this degradation at pH 7.2 and pH 8.6 easily measurable by the same measuring method of the optical density at the same pHs, it is easily checked that after the filling phase all the NADH which leaves the donor compartment D is to be found again in the receiver compartment R.

The experiment was continued until time $t=78$ hours for which the receiver compartment R titrates a concentration of 0.73 mM and the donor compartment D, a concentration 0.34 mM.

The "barriers" 5 have both a role of preventing the leakage of the enzyme molecules from the reactive membrane 6, thus playing a role of "molecular sieve", and of constituting, by reason of their charge, due to the presence of the Q-P(TDAE), partially quaternized to 14%, permselective membrane which is practically impermeable to $NAD^{30}$ and permeable to NADH, which explains qualitatively the active transport of the NADH from the D compartment into the R compartment.

Quantitatively the numeric simulation of the monoenzymatic reactive membrane system according to the present invention, was carried out by means of the diffusion-reaction equation:

$$\frac{\partial c_i}{\partial t} = D_i \frac{\partial^2 c_i}{\partial x^2} + R_i(c_k)$$

where:
$c_i$ is the concentration of the species i
t the duration
$D_i$ the diffusion coefficient of i
x the coordinates in space of the gel and
$R_i$ the speed of the enzymatic reaction involving i The estimate of the concentration profiles of the different species which pass through the membrane 6 and of the variations of the concentrations of NADH in the compartments D and R, given by numeric simulation, has proved to coincide with the experimental data which are shown in FIG. 4.

For this numeric simulation, the actual pH-dependances of the forward and back reactions have been smoothed by the equations:

$v = exp(-0.1966(pH-6)^2 + 9.453)$ for the forward reaction of optimal pH 6.0, and $v = exp(-0.2747(pH-8.2)^2 + 7.5)$ for the back reaction of optimal pH 8.2.

The diffusion coefficients have been determined experimentally (expressed in $dm^2/s$):

|  | reactive layer | barriers |
|---|---|---|
| NADH | $10^{-7}$ | $10^{-8}$ |
| $NAD^+$ | $10^{-7}$ | $3.10^{-11}$ |
| Aldehyde | $10^{-7}$ | $10^{-8}$ |
| Alcohol | $10^{-7}$ | $10^{-8}$ |

The Michaelian Kms were selected in accordance with the literature:

| $NAD^+$: 0.2 mM, | NADH: 0.02 mM |
|---|---|
| Alcohol: 20 mM; | Aldehyde: 0.2 mM |

The time increment was selected as 0.04 s.

The diffusion-reaction equations with partial derivatives have been applied to the species $NAD^{30}$, NADH and Aldehyde. The enzyme is considered as non-diffusing and the concentration of alcohol as constant in the whole system, by reason of its very high value with respect to the other concentrations.

EXAMPLE 2

To produce the accumulation and the concentration of the compound to be extracted, the method necessitates the existence of a reversible reaction between at least three reagents. Many enzymatic reactions being reactions with two reagents, for example those catalyzed by isomerases, we have shown that it was nonetheless possible to concentrate one of these reagents by blocking the complete enzymatic reaction and by limiting the chemical reaction to the reversible formation of the enzyme substrate complex. We then obtain the conventional diagram $E+S \rightleftarrows ES$ with three reagents E, S and ES. The two species E and ES are then confined to the intramembranal space by porosity barriers and an effector gradient, such as a proton gradient, creates the gradient of the active form of E, alone capable of bonding with S.

Thus yeast alcohol dehydrogenase (yADH) can fix the NADH by a non-ordinated mechanism:

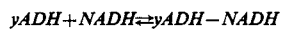

We have hence illustrated this mode of operation of the method based on the complexation enzyme-substrate by the extraction of the NADH by alcohol dehydrogenase, the blocking of the complete enzymatic reaction being effected by the absence of co-substrate This blocking, in the case of reactions with two reagents, can be done by the addition of inhibitors of the reaction.

Figure 5:
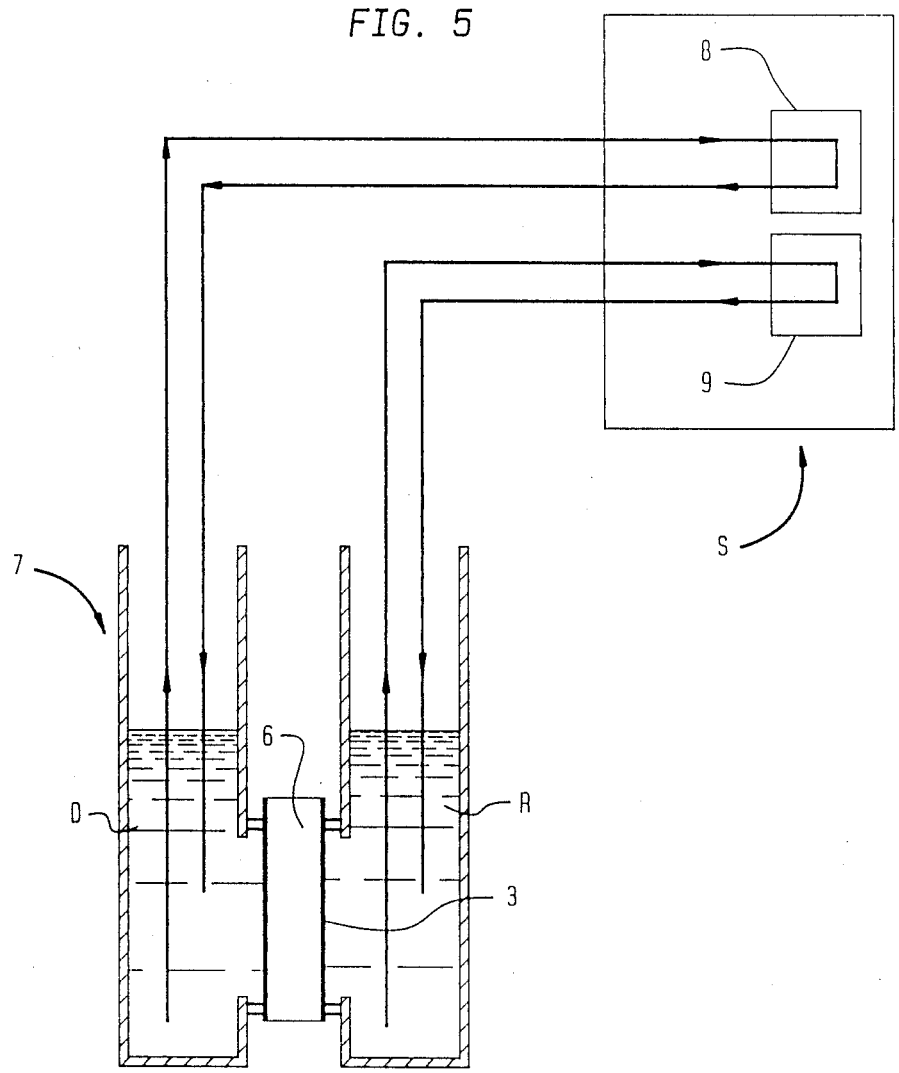

In accordance with the present invention, the system is composed as follows:

yADH is distributed homogeneously in a thin membrane (of the order of 1 mm thickness and 2 $cm^2$ surface area), 6, in 3.5% agarose gel in water containing 0.2 mg of yADH (namely 0.03 mM of enzymatic site/ml). The membrane is inserted between two microporous barriers 3 (for example of the Millipore type of porosity 0.025 $\mu m$ and of thickness 0.1 mm). The reactive membrane system so formed is placed in position in a cell 7 (cf FIG. 5) in which it defines two compartments, the compartment D (donor) and the compartment R (receiver), fluidtight with respect to one another. The two compartments contain initially the same buffered solution (phosphate buffer 100 mM) of NADH 0.15 mM.

Each compartment contains 10 ml of solution. At the initial time t=0, the pH of the compartments D and R is respectively adjusted to 7.5 and 8.3 by means of a pH-stat.

Figure 6:
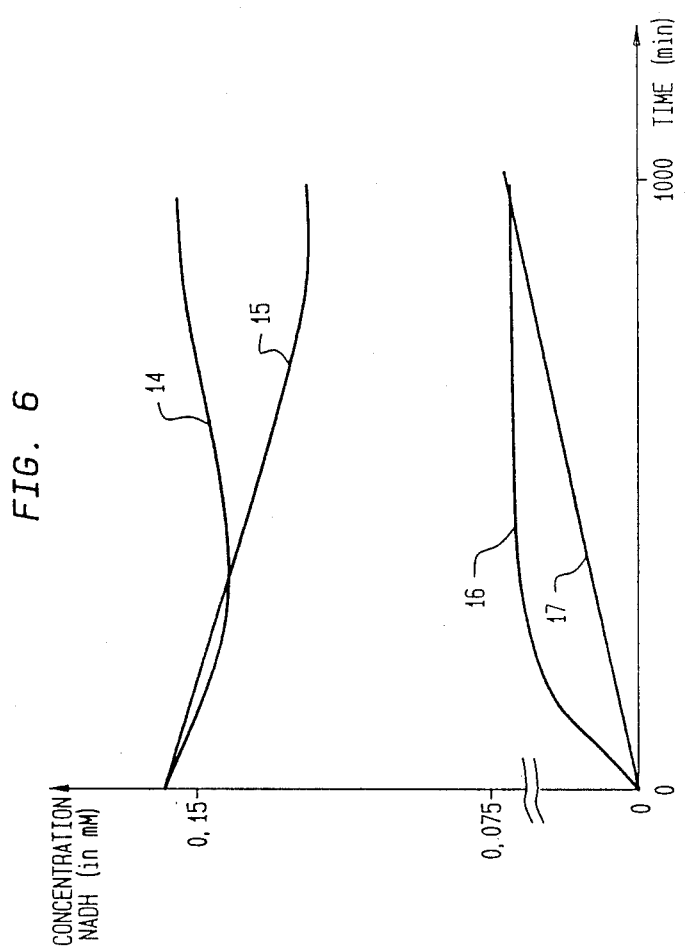

Two circulation cells 8 and 9, of a spectrophotometer S enable the continuous measurement of the optical density at 340 nm of the solutions contained in each of the compartments D and R, which varies proportionally with their concentration of NADH The curves of the concentrations of NADH in the two compartments read as a function of time, are shown in accompanying FIG. 6: they reveal, as in Example 1, the existence of two phases: the first, which corresponds to an asymmetric diminution of the concentrations of NADH in the two compartments, constitutes in fact the filling phase of the membrane (initially empty of NADH) as well as the establishment of the profiles of intramembranal concentration. This phase lasted about 400 minutes.

The second phase constitutes the active transport proper characterized by the increase in the concentration of NADH in the receiver compartment (pH 8.3) and the continuation of its diminution in the donor compartment (pH 7.5). These two developments are shown by the curves 14 and 15 The filling of the membrane is shown by the curve 16 and non-enzymatic destruction of the NADH at pH 7.5 by the curve 17. This degradation of the NADH has already been mentioned in Example 1.

After an overall time of 1,000 minutes, the difference between the two compartments in the concentration of NADH has reached 0.013 mM.

Numeric simulation on a computer confirms this type of experiment.

Example 3

Extraction of glucose by means of a membranal system comprising charged barriers The concentration of the glucose and the blocking of the G6P are obtained by using as barriers an agarose film containing polyacrylic acid which blocks the G6P by substantially reproducing the conditions described in Example 1 and by using hexokinase as catalyst.

Example 4

Amino-acid extraction by means of a membranal system comprising porosity barriers By using an active transport membrane carrying an exopeptidase, associated with neutral barriers constituted by micro-porous films (of the Millipore type for example), the synthesis-enzymatic cut-off of proteins is performed to extract specific amino-acids, which pass through the micro-porous films, whilst the peptides from which the amino-acids are cut-off do not pass through said films.

$Peptide_n \rightleftarrows peptide_{n-1} + amino\text{-}acid$

Example 5

Extraction of adenine

By a membrane of agarose gel carrying adenine-phosphoribosyl-transferase, limited by hydrophobic barriers, adenine is extracted, it also hydrophobes by giving the hydrophile intermediate AMP The preceding examples show that the invention encompasses the most diverse reversible enzymatic reactions.

The preceding examples show also that the invention encompasses barriers which prevent one of the components of the reaction to emerge from the membrane, this by modifying the electrical charge of the barrier, the porosity or again its hydrophobicity.

In the same way, the invention encompasses the uses of this method in reactors of discontinuous type, as well as in continuous flow reactors. The invention is also applicable to plurienzymatic systems.

We claim:

1. A method of selective extraction of a compound from a complex solution comprising:

introducing said solution into a system comprising a cell subdivided into two compartments by a reactive membrane system, said two compartments comprising donor compartment D and receptor compartment R;

said reactive membrane system comprising a membrane structure carrying enzymatic catalysts which confer enzymatic activity on said membrane structure, a first barrier layer provided on a first surface of said membrane, and a second barrier layer provided on a second surface of said membrane, said barrier layers adapted to prevent the passage through said active membrane of substance other than the compound to be extracted;

transporting the compound to be extracted from donor compartment D to an intramembranal space containing a liquid medium, using a monoenzymatic reactive membrane system suitable for catalyzing a reversible reaction;

wherein in said intermembranal space are contained at least the compound to be extracted;

establishing an electrochemical potential gradient of said at least one compound, said gradient creating asymmetric functional conditions which conditions force the reversible reaction to be conducted in one direction on one side of the reactive membrane system and in the other direction on the other side of the reactive membrane system; providing means for providing an alternative to a pressurization means including a reaction loop which makes said compound to be extracted pass from the one side of the reactive membrane to the other side of the reactive membrane, said compound to be extracted accumulates on said other side of said reactive membrane, wherein said transport is facilitated by the presence on one of the two side of said membrane a layer facilitating transport intermembranal space at least one compound other than said compound to be extracted; and recovering said compound to be extracted in receptor compartment R.

2. The method according to claim 1 wherein the layer comprising a barrier is a structure which prevents passage of the compound to be confined in the intramembranal space.

3. The method according to claim 2 wherein when the compound to be confined is charged, the barrier carries an overall charge of the opposite sign.

4. The method according to claim 2 wherein when the compound to be confined is a large molecule, the barrier comprises a microporous film.

5. The method according to claim 2 wherein when the compound to be confined exhibits a given hydrophobicity, the barrier comprises a substance conferring on said barrier a hydrophobicity of opposite nature.

6. The method according to claim 1 wherein the ratio of the diffusion coefficients $$\frac{\text{compound to be extracted}}{\text{compound to be confined in the intramembranal space}}$$

7. The method according to claim 1 wherein when the reaction involves at least three reagents, including a reagent to be extracted, at least one co-reagent, and at least one compound intended to be confined in the intramembranal space defined by the membranal system, the electrochemical potential gradient of the co-reagent or of one of the coreagents is established, for a given equilibrium constant $K_{eq}$, by adjusting the electrochemical potentials to different values in the receptor and donor compartments defined by the membranal system, on each side of the membranal system, so that the ratio K given by the law of mass action, in which the concentration of the compound to be extracted is in the denominator, is
$K < K_{eq}$ on the donor side and
$K > K_{eq}$ on the receptor side.

8. The method according to claim 1 wherein when the reaction involves protons, the protons are used as the reagent for which it is desired to establish the gradient by adjusting the pH of the donor compartment to be different from the pH of the receptor compartment.

9. The method according to claim 1 wherein when the reaction involves at least two reagents, said two reagents comprising a compound to be extracted and a reagent, a complex is formed between the compound to be extracted and the enzyme, and both the enzyme and the enzyme-compound complex are confined in the intramembranal space, and an intermediate gradient of a suitable effector is established as a pH gradient, so as to cause in the intramembranal space the establishment of an active free enzyme gradient which is the desired electrochemical potential gradient.

10. The method according to claim 1 wherein in the case in which the enzymatic reaction involves at least two reagents of the type A=B, the chemical potential wherein it is applied to the compound to be extracted, the energy source comprising the dissipation of this gradient to form a facilitated transport which selectively increases the speed of passage through the membrane of the compound to be extracted.

11. The method according to claim 1 wherein in the case in which the enzymatic reagent involves a plurality of reagents, there is formed and decomposed an enzyme-compound to be extracted complex $E+A=EA$ and the enzyme itself is used, in free or complexed form, as the substance confined in the intramembranal space, in which case the gradient is obtained by an effector gradient to form an active transport.

12. The method according to claim 11 wherein the gradient is obtained by using the compound to be extracted to form a facilitated transport which selectively accelerates the diffusion of the compound to be extracted.

13. Apparatus for the selective extraction of a compound with high added value form a complex solution, said apparatus comprising a cell subdivided into two compartments by a reactive membrane system;
said reactive membrane system comprising a membrane structure carrying enzymatic catalysts;
said membrane structure provided with a first barrier layer on a first surface and a second barrier layer on a second surface, said first and second barrier layers adapted to prevent the passage through said active membrane of substances other than the compound to be extracted;
said active membrane comprises a thin layer of a gel carrying a single enzymatic catalyst;
means for providing an alternative to a pressurization means including
said first and second barrier layers which introduce a difference of mobility thorough the membranal reagent system between the compound to he extracted and at least one of the other reagents present.

14. Apparatus according to claim 13 wherein said cell is of the closed reactor type suitable for discontinuous operation.

15. The apparatus according to claim 13 wherein said cell is of the closed reactor type suitable for discontinuous operation.

16. The apparatus according to claim 13 wherein said enzymatic catalyst is retained in the membrane by means of a microporous film on said first and second surfaces of said membrane.

17. The apparatus according to claim 13 wherein said enzymatic catalyst is fixed by covalent bonding to the membrane which carries said catalyst.

* * * * *